United States Patent [19]

Columbus et al.

[11] Patent Number: 4,988,341

[45] Date of Patent: Jan. 29, 1991

[54] STERILIZING DRESSING DEVICE AND METHOD FOR SKIN PUNCTURE

[75] Inventors: Richard L. Columbus; Thomas R. Kissel, both of Rochester, N.Y.

[73] Assignee: Eastman Kodak Company, Rochester, N.Y.

[21] Appl. No.: 361,473

[22] Filed: Jun. 5, 1989

[51] Int. Cl.⁵ .............................................. A61F 13/00
[52] U.S. Cl. .................................. 604/306; 128/888; 604/304; 604/307
[58] Field of Search ...................... 604/19, 48, 51, 52, 604/171, 173, 174, 180, 181, 199, 263, 304, 306, 307, 200, 244; 128/155, 156, 888

[56] References Cited

U.S. PATENT DOCUMENTS 3,367,332  2/1968  Groves ........................... 128/156 X
3,782,377  1/1974  Rychlik .............................. 128/888
3,900,026  8/1975  Wagner .............................. 128/888

Primary Examiner—Alan Cannon
Assistant Examiner—Elizabeth Burke
Attorney, Agent, or Firm—Dana M. Schmidt

[57] ABSTRACT

A dressing device and method are described, for use with a needle that is injected into the skin. The dressing device comprises a cover sheet and a gel medium attached to the cover sheet, the gel medium being transparent and effective to reseal after being punctured by the needle. Most importantly, the gel medium includes a sterilizing agent.

Injection of the needle into the skin occurs only after the needle penetrates the gel medium, so that the needle is disinfected or sterilized.

4 Claims, 1 Drawing Sheet

STERILIZING DRESSING DEVICE AND METHOD FOR SKIN PUNCTURE

FIELD OF THE INVENTION

This invention relates to dressing device and a method used to prevent infection of a live host body during injection to remove blood or inJect a medicament.

BACKGROUND OF THE INVENTION

The conventional procedure by medical practitioners for drawing blood from, or injecting a substance into, a live host body, has been for years to do the following steps:

1. Sterilizing the skin to be punctured by vigorous abrasive rubbing with an alcohol swab,
2. removing a needle or cannula from a needle case and inserting it into a syringe holder fitted with a vacutainer or a drug containing syringe,
3. injecting through the skin in the swabbed area and drawing blood or injecting a drug,
4. destroying the needle,
5. removing and labeling of the vacutainer containing the sample (if blood has been taken),
6. swabbing the wound to disinfect and remove blood leaking from the wound, and
7. covering the wound with a covering.

This practice continues, even though it is now well recognized that alcohol swabbing of the skin is inadequate protection from infection. Not only is the alcohol swab deficient in skin cleansing, but also the cannula can be contaminated and require cleansing. Alcohol is bactericidal against vegetative forms of bacteria through the denaturation of cellular proteins; however, it is far from ideal as a skin or surface disinfectant. Alcohol is flammable, it evaporates too fast to be very effective (it should remain on the skin surface for about 10 minutes), and it dries and irritates the skin.

It would thus be highly desirable to provide a means for sterilizing human skin prior to venipuncture, without abrasion, and in the same step provide protection from infection of the patient by the needle and continued protection of the patient after injection while minimizing the potential of infection of others by the patient's blood as a result of aerosols, leakage from the wound, handling of a swab before dressing the wound, or leakage from the cannula.

Some early attempts have been made to provide alternate procedures. For example, U.S. Pat. No. 3,367,332 (1968) teaches the use of a resealable patch and membrane bandage through which the needle is inserted (FIG. 3), at least the bandage having been sterilized with an antiseptic prior to injection of the host. However, the patch does not contain a sterilizing agent, so that the needle encounters only a thin layer of the sterilizing agent presented by the membrane. Furthermore, although the membrane may be thin and transparent, the patch is not and has substantial thickness, so that the phlebotomist is unable to correctly identify the injection site by sight or by feel, through the patch. In the case of a blood draw, stabbing "in the dark" is unacceptable. For these and other reasons, the technology of this patent has failed to replace the traditional use of alcohol swabs, deficient though the latter might be.

Thus, prior to this invention there has been a need for a sterilizing medium to be used with a needle, and a method of phlebotomy or drug injection, that more adequately sterilizes the needle while permitting precise location of the inJection site.

SUMMARY OF THE INVENTION

We have devised a sterilizing device and method that overcome the above noted disadvantages.

More specifically, in accord with one aspect of the invention there is provided a sterilizing device for use with a needle to inJect into or remove a liquid from a site on a live host body, the device comprising: a transparent, puncturable, resealable gel medium containing a sterilizing agent preincorporated therein, the medium being constructed to cover the site; a non absorbent protective cover on one side of the medium having margin portions extending beyond the outside margin of the medium; means for retaining the medium to the cover; and adhesive disposed on surface portions of the extending portions of the cover, the adhesive being disposed for exposure and contact of the host body when the medium is exposed and in contact with the host body.

In accord with another aspect of the invention, there is provided a method of injecting liquid into, or removing liquid from, a site on a live host body. The method comprises (a) positioning a transparent, puncturable, resealable gel medium containing a sterilizing agent preincorporated therein, to cover the site, said medium having adhesive at least partially surrounding it and positioned to temporarily hold the medium on the host body; (b) contacting the body site with the medium and adhesive; and (c) inserting a needle into the host body by injecting the needle first through the medium so as to contact the sterilizing agent; whereby sterility of the needle is insured.

The gel medium of this invention is considered superior because it is transparent, admixes well with the sterilizing agent, provides no objectionable contaminant of the host, and is manipulatable enough to allow the site, at least in the case of a vein, to be identified by feel. This is in contrast to alternative media such as fibers, which tend to interfere both with seeing the site and feeling the site, for the inJection. Furthermore, fibers can be objectionable if the needle inadvertently injects one of them into the host.

Accordingly, it is an advantageous feature of this invention that a medium properly sterilizes both the skin of the host to be penetrated and the penetrating instrument, without interfering with the proper detection of the injection site.

It is another advantageous feature of the invention that a sterilizing medium and method are provided that are free of the use of alcohol and its attendant disadvantages.

Other advantageous features will become apparent upon reference to the Detailed Description of the Preferred Embodiment, when read in light of the attached drawings.

DESCRIPTION OF THE PREFERRED EMBODIMENTS

Figure 1:
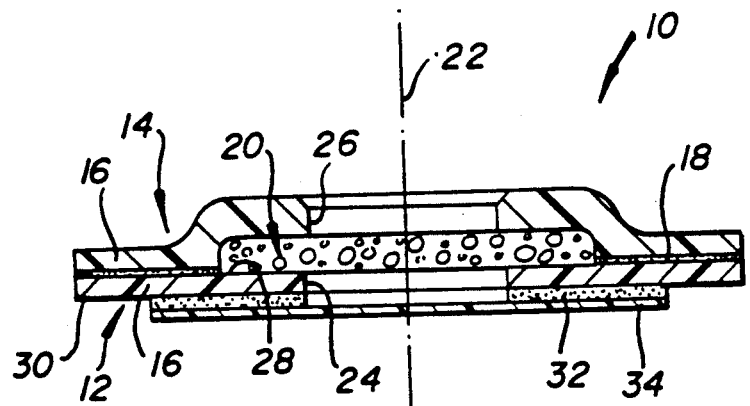
FIG. 1 is an elevational view in section of a sterilizing dressing medium constructed in accord with the invention.

The invention is hereinafter described with respect to a dressing used with a needle to draw blood from a site, a preferred embodiment. In addition, it is useful with a syringe needle used to inject medicaments into a site.

As is customary with skin dressings, the device 10 of the invention comprises a first non-absorptive cover or base portion 12, a second non-absorptive cover or top portion 14 permanently affixed along margin portion 16 only, to the first cover by means such as an adhesive layer 18, and a medium 20 sandwiched between the two covers. All three are most preferably symmetric about the center axis 22, that is, are generally disc shaped. Both covers 12 and 14 are preferably apertured at 24 and 26, respectively, for reasons which will become apparent. It is the non attached inside margin portions 28 of covers 12 and 14 that hold medium 20 in place.

The outer surface 30 of cover 12 has at least a portion thereof coated with a conventional releasable adhesive 32 suitable for contact with skin. As sold, device 10 includes a plastic, paper, metal foil or a laminate release sheet 34 adhered to adhesive 32, until that sheet is peeled away by the user to allow the device to be stuck to the skin. Sheet 34 is preferably a solid disk having a shape and size effective to cover adhesive 32.

Conventional plastics or plastic-covered paper, metal foil or laminates can be used for covers 12 and 14.

In accordance with one aspect of the invention, medium 20 comprises a transparent, resealable, puncturable gel that contains throughout its volume, a sterilizing agent preincorporated therein. As used herein, "sterilizing agent" is any anti-bacterial agent, fungicide, anti yeast agent or anti-viral agent or combination thereof. The selection, of course, is dependent upon the end use, a combination of an anti-viral agent and a anti-bacterial agent being preferred. Useful examples include parachlorometaxylenol (PCMX), chlorhexidine gluconate (CHG), triclosan, alcohol, iodophores and povidone-iodine, Nonoxynol-9 TM, phenolic compounds, quaternary ammonium compounds, chlorine solutions (sodium hypochlorite or chlorine dioxide), and glutaraldehyde. In addition, a topical anesthetic is optionally included, for example, benzocaine, xylocaine, menthol, pramoxine or dimethisoquin, which is effective upon contact with the skin.

Any gel material is useful for medium 20 if it provides the above functions. Most preferred is a hydrogel that is an interlaced network of agar and a copolymer of acrylamide crosslinked with the monomer N, N' - methylenebisacrylamide, and 96 by weight %, bound water. A preferred example is the gel sold by Geistlich Pharma of Switzerland under the trademark "Geliperm" TM. Other useful examples include gels that are copolymers of 2-hydroxyethyl methacrylate. The water is essential to keep the polymer network expanded, and to disperse the sterilizing agent. The polymer network serves to hold the liquid in place. The net result is a medium that is transparent, has no fibers to be inJected into the skin, and distributes the sterilizing agent throughout. Thus, no matter which portion of medium 20 is penetrated by the needle, the agent will be effective to sterilize the needle.

Although for ease in manufacturing, the sterilizing agent is preferably dispersed throughout the medium, the sterilizing agent will also function if it is located primarily at the upper and lower surfaces of the medium, that is, where the needle and the skin encounter the gel medium.

The gel is also effective to reseal when the needle is withdrawn, and to wipe the needle of any blood on its exterior. The sterilizing agent is preferably effective to sterilize any harmful virus or bacteria that might remain on the removed needle, for example, the HIV-1 virus or hepatitis-B virus that can be present in the blood withdrawn by the needle.

The thickness of medium 20 is not critical, other than it must be sufficiently thick as to hold together, and thin enough to permit the user to feel the skin underneath. For example, 100 microns is useful.

Figure 2:
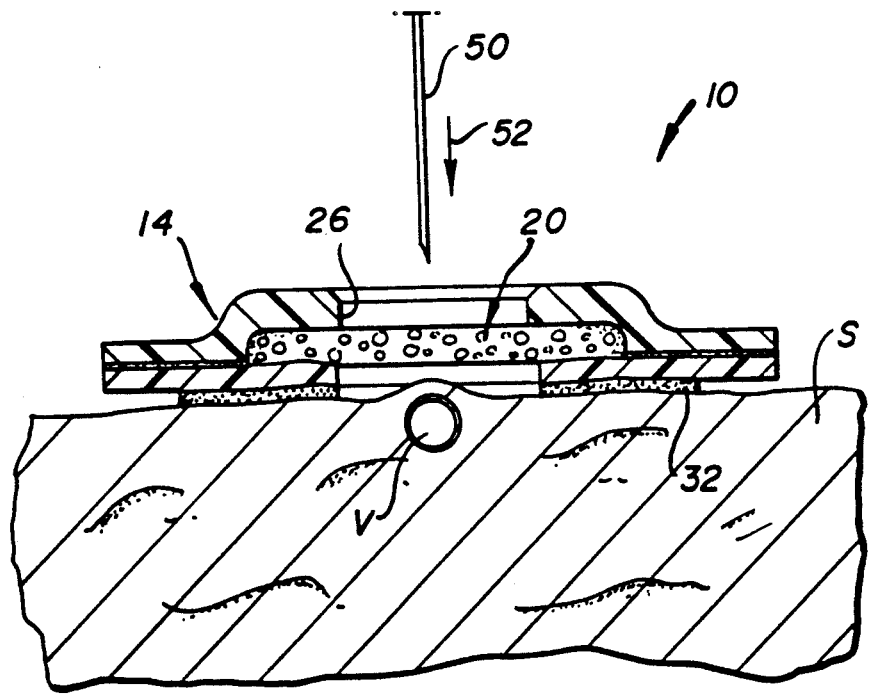
FIG. 2 is a view similar to that of FIG. 1, illustrating the use of the invention.

The purpose of aperture 26 will become more apparent in the description of the use of the device 10, FIG. 2. That is, release sheet 34 is stripped off and discarded, thus exposing both adhesive 32 and gel medium 20 to the skin S to which device 10 is to attach. Device 10 is maneuvered to cover the site of the needle puncture, and to this end, aperture 26 or its equivalent is used to aid in finding the proper site. For example, vein V :an be seen through aperture 26 and the transparent medium 20, and properly located vis-a-vis medium 20. In addition, the vein V can be felt through medium 20, since it is devoid of fibers that could camouflage the feel of the vein's location.

After medium 20 is properly located on the site, medium 20 is preferably massaged onto the site to disperse the sterilizing agent over the site. Such massaging further confirms the proper location by the sense of touch.

After device 10 is in contact with skin S at the site, a needle 50 is positioned at aperture 26, and then inserted via arrow 52 first (not shown) through medium 20 and then into the skin S.

Thus, an equivalent to aperture 26 in cover 14 is a transparent portion (not shown) of the cover that physically covers medium 20 in its entirety, while still making it possible to see and feel through device 10 to the site. In such a case, device 20 is fully covered and protected against premature exposure of medium 20. Alternatively, if aperture 26 is present as such, the entire device is wrapped and stored in protective plastic.

Preferably, device 10 is thrown away after a single use. However, and particularly if used with a syringe to deliver a medicament, because of the gel nature of medium 20, device 10 can be reused if a second injection is to occur elsewhere on the patient. That is, when the needle is withdrawn the gel completely reseals, and becomes an integral member in which the sterilizing agent is still uniformly dispersed. Thus, additional needles can penetrate the same medium, without fear of the sterilizing agent no longer being effective.

Other agents can be optionally added to medium 20 as desired, for particular applications. For example, perfumes, silicones, antioxidants, and even coagulating agents can be added.

The invention has been described in detail with particular reference to preferred embodiments thereof, but it will be understood that variations and modifications can be effected within the spirit and scope of the invention.

What is claimed is:

1. A sterilizing device for use with a needle to inject into or remove a liquid from a site on a live host body, said device comprising:

a transparent, puncturable, resealable gel medium containing a sterilizing agent preincorporated therein, said medium being constructed to :over said site;

a non-absorbent protective cover on one side of said medium having margin portions extending beyond the outside margin of said medium;

means for retaining said medium to said cover;

and adhesive disposed on surface portions of said extending portions of said cover, said adhesive being disposed for exposure and contact of said host body when said medium is exposed and in contact with said host body.

2. A device as defined in claim 1, wherein said retaining means comprise a second protective cover adhered to said one side protective cover with said gel medium sandwiched between them, said second cover being capable in a portion thereof of visual examination of said gel medium and site underneath it.

3. A device as defined in claim 1, wherein said gel medium comprises an interlaced network of agar and an acrylamide copolymer.

4. A device as defined in claim 1, wherein said sterilizing agent is an agent selected from the group consisting of an anti-bacterial agent, a fungicide, an anti-yeast agent, an antiviral agent and mixtures thereof.

* * * * *